(12) United States Patent
Tsukamoto et al.

(10) Patent No.: US 8,193,003 B2
(45) Date of Patent: Jun. 5, 2012

(54) METHOD AND SYSTEM FOR DETECTION OF BIOMATERIALS USING MAGNETIC MARKER

(75) Inventors: Akira Tsukamoto, Toda (JP); Daisuke Suzuki, Kokubunji (JP); Akihiko Kandori, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 761 days.

(21) Appl. No.: 12/149,990

(22) Filed: May 12, 2008

(65) Prior Publication Data

US 2008/0284413 A1 Nov. 20, 2008

(30) Foreign Application Priority Data

May 17, 2007 (JP) .................................. 2007-131203

(51) Int. Cl.
*G01N 33/553* (2006.01)
*G01N 33/53* (2006.01)
(52) U.S. Cl. ........................................ 436/526; 435/7.1
(58) Field of Classification Search .................. 436/526; 435/7.1
See application file for complete search history.

(56) References Cited

U.S. PATENT DOCUMENTS

| | | | |
|---|---|---|---|
| 6,027,946 A | 2/2000 | Weitschies et al. | |
| 2005/0202572 A1 | 9/2005 | Seki et al. | |
| 2007/0155024 A1* | 7/2007 | Miethe et al. | 436/524 |
| 2007/0207553 A1* | 9/2007 | Fox | 436/501 |
| 2008/0024117 A1* | 1/2008 | Hong et al. | 324/201 |

FOREIGN PATENT DOCUMENTS

| | | |
|---|---|---|
| JP | 63-90765 | 10/1986 |
| JP | 03-220442 | 1/1990 |
| JP | 10-513551 | 1/1996 |
| JP | 2001-33455 | 7/1999 |
| JP | 2001-133458 | 11/1999 |
| JP | 2005-257425 | 3/2004 |

OTHER PUBLICATIONS

Y.R. Chemla et al.; "Ultrasensitive Magnetic Biosensor for Homogeneous Immunoassay"; Dec. 19, 2000; Proc. National Academy Sciences of U.S.A.; vol. 97, No. 26, pp. 14268-14272.

A. Haller et al.; "Low $T_c$ SQUID Measurement System for Magnetic Relaxation Immunoassays in Unshielded Environment"; Mar. 2001; IEEE Transactions on Applied Superconductivity, vol. 11, No. 1, pp. 1371-1374.

H.L. Grossman et al.; Detection of Bacteria in Suspension by Using a Superconducting Quantum Interference Device; Jan. 6, 2004; Proc. National Academy Sciences of U.S.A.; vol. 101, No. 1, pp. 129-134.

(Continued)

*Primary Examiner* — Mark Shibuya
*Assistant Examiner* — Pensee Do
(74) *Attorney, Agent, or Firm* — Stites & Harbison, PLLC; Juan Carlos A. Marquez, Esq (57) ABSTRACT

Accurate measurement cannot be performed due to magnetic signals from magnetic impurities included in a specimen container. By finding a difference between two measurement signals obtained by applying an external magnetic field for orientation to respective normal and reverse directions, the magnetic signals from the magnetic impurities included in the specimen container which are not dependent on the external magnetic field for orientation can be cancelled. The influence of the magnetic impurities included in the specimen container is reduced, and the signal of the intended bound magnetic marker can be measured with high sensitivity.

3 Claims, 9 Drawing Sheets

OTHER PUBLICATIONS

K. Enpuku et al.; High $T_c$ SQUID System and Magnetic Marker for Biological Immunoassays; Jun. 2003; IEEE Transactions on Applied Superconductivity, vol. 13, No. 2, pp. 371-376.

R. Kötitz et al.; SQUID Based Remanence Measurements for Immunoassays; Jun. 1997; IEEE Transactions on Applied Superconductivity, vol. 7, No. 2, pp. 3678-3681.

* cited by examiner

FIG. 1

(A) BINDING REACTION (B) MAGNETIZATION (C) APPLICATION OF MAGNETIC FIELD FOR ORIENTATION (FORWARD DIRECTION)

(D) MEASUREMENT OF MAGNETIC SIGNAL (SIGNAL 1)

(E) APPLICATION OF MAGNETIC FIELD FOR ORIENTATION (REVERSE DIRECTION)

(F) MEASUREMENT OF MAGNETIC SIGNAL (SIGNAL 2)

METHOD AND SYSTEM FOR DETECTION OF BIOMATERIALS USING MAGNETIC MARKER

CLAIM OF PRIORITY

The present application claims priority from Japanese application JP2007-131203 filed on May 17, 2007, the content of which is hereby incorporated by reference into this application.

BACKGROUND OF THE INVENTION

The present invention relates to a system that analyzes biological substances and the like by a magnetic signal by using magnetic nano particles and a magnetic sensor, for example, an immunoassay system used for inspection of, for example, immunoglobulin, hormone, a tumor marker, infectious diseases or the like, a blood culturing device and a bacterial culturing device used for inspection of pathogenic bacterium of an infectious disease, food poisoning and the like.

Inspection of various biological substances (hormone, antibody, antigen, tumor markers and the like), pathogenic bacterium, viruses, cancer cells, DNA, environmentally hazardous materials and the like is possible by using specific binding reaction such as antigen-antibody reaction. In recent years, there has been a growing demand for quick and highly sensitive detection of these inspection targets, and the immunoassay systems for this purpose have been energetically developed. As a general method of immunoassay, there is an optical method in which an antibody for detection which selectively adheres to the antigen to be a detection target is marked with an optical marker such as a luminescence enzyme or the like, the binding reaction of antigen and the antibody is detected by detecting an optical signal from the optical marker, and the kind and quantity of the antigen are detected. However, in the optical method, the detection sensitivity is not sufficient, and the process of washing the unbound optical marker (washing process) is required.

In recent years, a magnetic method for detecting an antigen-antibody reaction by using magnetic nano particles and a magnetic sensor has been proposed. In the magnetic method, an antibody magnetically marked with magnetic nano particles (hereinafter, called a magnetic marker) is bound to the substance of the detection target, and the magnetic signal generated from the bound magnetic marker is detected by using a magnetic sensor. By using a Superconducting quantum interference device (SQUID) which is a highly sensitive magnetic sensor, detection sensitivity higher than that of the optical method is obtained.

There are proposed various methods for detecting biomaterials by magnetic signals with magnetic nano particles as labels.

In the method disclosed in JP-61-235774, a substance to be measured is fixed to a container and thereafter, is reacted with a magnetic marker, and after the unbound magnetic marker is washed, a residual magnetic signal from the magnetic marker which is bound to the substance to be measured fixed to the container is measured with a SQUID.

In the method disclosed in JP-2-15551, by mixing the solution containing a substance to be measured and magnetic markers in a solution, the substance to be measured and the magnetic markers are bound to form an aggregate, and after in the state where unbound magnetic markers exist, an external magnetic field is applied to align the directions of the magnetic markers, the magnetic signal after the magnetic field is shut off is measured. The directions of the magnetic moments of the magnetic markers in suspension in the solution become random due to Brownian motion, and therefore, even when the directions of the magnetic moments are aligned by the magnetic field, if the magnetic field is shut off, the magnetic signal gradually decays. When the magnetic markers bind with the target substance and aggregate, the volume as a rotating body increases, and therefore, decaying time of the magnetic signal is delayed, but the magnetic signal of the unbound magnetic marker decays early. Since the relaxation time constant of the magnetic signals differ, the magnetic signal of the bound marker can be measured without removing the unbound marker. Similar methods are also reported in Y. R. Chemla, et al.: Proc. National Acad. Sciences of U.S.A. 97, 14268 (2000), A. Haller, et al.: IEEE Trans. Appl. Supercond. 11, 1371 (2001), H. L. Grossman, et al.: Proc. National Acad. Sciences of U.S.A. 101, 129 (2004) and JP-A-10-513551.

In the methods of JP-A-2005-257425 and K. Enpuku, et al.: IEEE Trans. Appl. Supercond. 13, 371 (2003), the substance to be measured is fixed to the container, and thereafter, caused to react with a magnetic marker, and a signal from the magnetic marker bound to the substance to be measured which is fixed to the container in the state in which an unbound magnetic marker exists is measured with a SQUID magnetic sensor. The directions of the magnetic moments of the unbound magnetic markers become random due to Brownian motion, and therefore, the magnetic signals decay. Therefore, the signal from the bound magnetic marker can be measured without washing the unbound marker. A similar method is also reported in R. Kotitz, et al.: IEEE Trans. Appl. Supercond. 7, 3678 (1997).

In JP-A-2001-33455 and JP-A-2001-133458, methods using susceptibility measurement are reported. In JP-A-2001-33455, a DC magnetic field which magnetizes the magnetic marker is applied from the direction orthogonal to the magnetic flux detecting direction of a SQUID magnetic sensor, and the change in the magnetic field caused by the magnetic markers which move in the magnetic flux detection region of the SQUID magnetic sensor is measured. In JP-A-2001-133458, an AC magnetic field is applied to the magnetic marker, and antigen-antibody reaction is detected by detecting the signal by using a SQUID magnetic sensor.

As above, magnetic signals from the bound magnetic markers are measured by the various methods, but the measured magnetic signals include external ambient magnetic signals, magnetic signals from magnetic impurities included in the containers, and magnetic signals from the magnetic markers nonspecifically bound to the containers, as noise signals. In order to make highly accurate measurement, it is necessary to reduce these magnetic signals.

As described above, the measured magnetic signals include not only signals from the bound magnetic marker and unbound magnetic marker, but also a noise signal of the sensor itself, external ambient magnetic signals, magnetic signals from the magnetic impurities included in the container, and magnetic signals from the magnetic markers nonspecifically bound to the container. In order to make measurement with high accuracy, these magnetic signals need to be reduced.

In the manufacturing process of the container, it is extremely difficult to suppress inclusion of magnetic impurities completely even if the containers are produced with close attention paid to the raw material, production process and the like. Even if magnetic impurities are not included in the container itself, dust and the like which are magnetized are likely to adhere to the container bottom surface and the like.

In the optical method, such contamination of the container does not become a problem. The substance used for an optical marker such as phosphors does not exist in an ordinary manufacturing process and use environment, and is not included in or does not adhere to the container. However, in an ordinary environment, a number of substances having magnetism exist. Therefore, impurities and contamination of the container are new problems peculiar to magnetic detection.

Meanwhile, nonspecific binding of markers to the containers also becomes a problem in optical methods. The container surface is usually coated with a blocking agent such as a BSA for preventing nonspecific binding, but it is difficult to prevent nonspecific binding of a marker completely. Especially in the inspection system of the method in which the measuring container is reused by washing, for example, of a flow cell method, washing is performed a plurality of times in order to remove the marker adhering to the measuring container, but it is difficult to remove it completely with favorable reproducibility, and this becomes the factor that restricts the lower limit concentration of detection.

BRIEF SUMMARY OF THE INVENTION

An object of the present invention is to provide an inspection technique which cancels magnetic signals from magnetic impurities included in a container or adhering to a container surface and a magnetic marker nonspecifically bound to the container (hereinafter, they will be called magnetic impurities bound to the container), and is not influenced by the magnetic signals from them.

The present inventors have found out that in the case of magnetic measurement without using a capturing antigen for fixing a substance to be measured to the container, an unbound magnetic marker and magnetic impurities bound to the container are removed from the measurement signals, and the signal of the bound magnetic marker can be measured with high accuracy. This is applicable to the measuring methods of, for example, JP-2-15551, JP-A-10-513551, Y. R. Chemla, et al.: Proc. National Acad. Sciences of U.S.A. 97, 14268 (2000), A. Haller, et al.: IEEE Trans. Appl. Supercond. 11, 1371 (2001) and H. L. Grossman, et al.: Proc. National Acad. Sciences of U.S.A. 101, 129 (2004).

Figure 1:
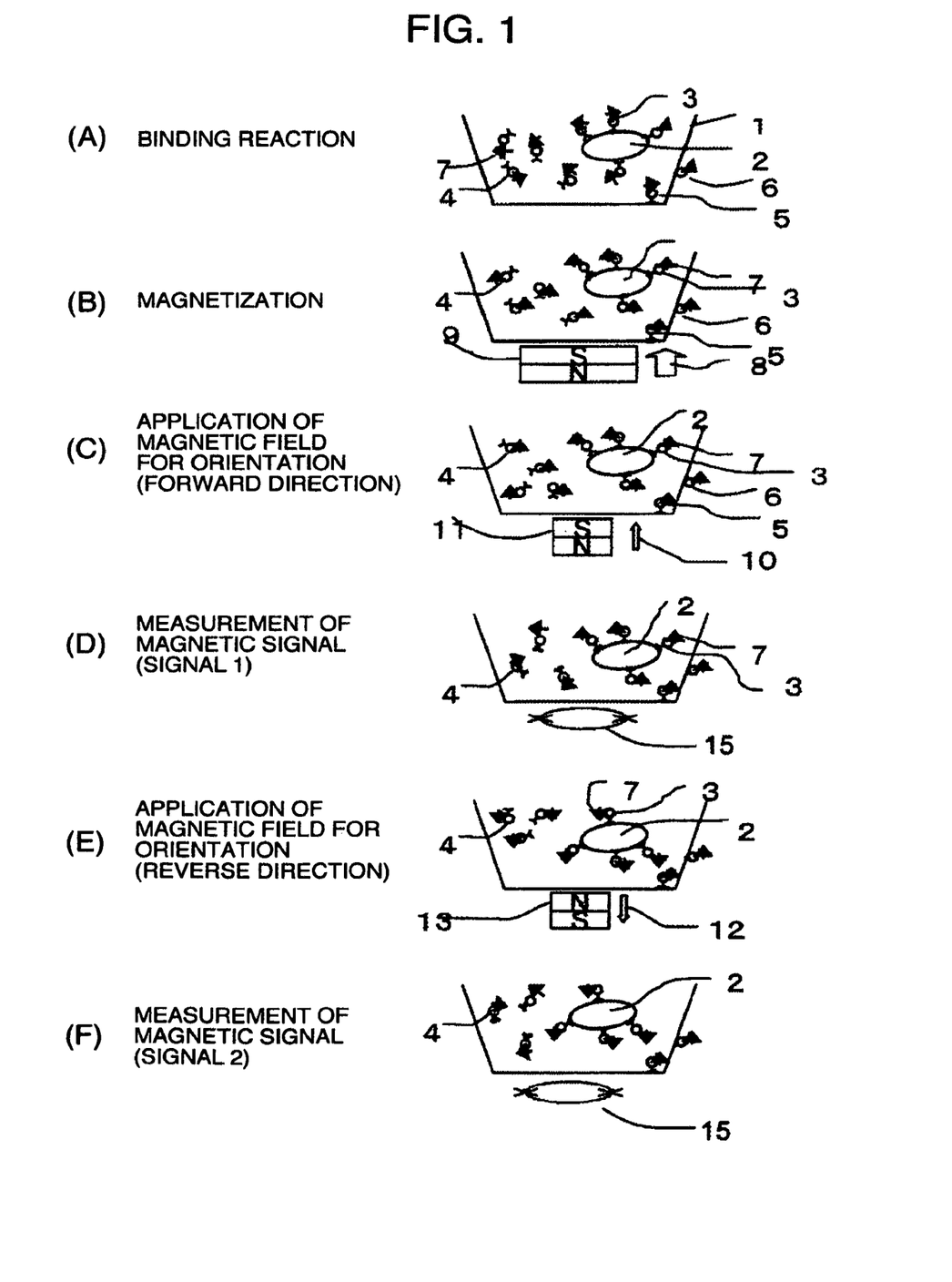
FIGS. 1A to 1F are explanatory views of a measurement procedure using a method of the present invention.

FIG. 1 schematically shows an example of a measurement procedure using the method of the present invention. In FIG. 1, a cell having a plurality of binding sites on the surface, for example, a leukocyte or pathogenic bacteria is shown as an example as the substance to be measured, but in the present invention, other substances that are substances capable of being measured by binding assay such as an antibody, hormone, protein and DNA, for example, are also the targets of measurement.

(a) A solution specimen including a measurement target substance 2 (for example, a serum) and magnetic particles (magnetic marker) to which a substance (antibody) to be specifically bound to the measurement target substance is fixed are added to a specimen container 1. Part of the added magnetic marker binds with a binding region of the measurement target substance 2. Hereinafter, the magnetic marker which is bound to the measurement target substance will be called a bound magnetic marker 3. Further, the magnetic marker dispersed in the solution without being bound will be called an unbound magnetic marker 4. Some magnetic markers nonspecifically adheres to a container wall surface. Such magnetic markers will be called nonspecific binding magnetic markers 5. Further, magnetic impurities which include a magnetic impurity 6 which is likely to be included in the container or adhere to the surface is also shown in the drawing. The small arrows shown in the drawing indicate the directions 7 of the magnetic moment. In this stage, the directions of the magnetic moments are not aligned in one direction, and therefore, the magnetic signal is relatively weak. In this state, measurement can be performed by applying a magnetic field for orientation, but a stronger magnetic signal can be expected when the magnetization is performed before measurement with a strong magnetic field like a saturated magnetic field, by applying a magnetic field for magnetization as described next.

(b) An external magnetic field 8 for magnetization is applied by using a magnet 9 to magnetize the magnetic marker. At this time, in the unbound magnetic marker 4, the particles themselves can rotate so that the magnetic moment thereof is directed along the direction of the external magnetic field 8 for magnetization. Meanwhile, a plurality of the magnetic markers bound to the measurement target substance 2 cannot independently rotate, but by applying a strong magnetic field, the direction of the spin in the magnetic nano particles changes to be along the direction of the external magnetic field 8 for magnetization, so that the directions of the magnetic moments of a plurality of the magnetic markers bound to the measurement target substance can be aligned with one direction. The strength is about the magnetic field necessary for saturated magnetization. At this time, the magnetic impurities are also magnetized and has the magnetic moment along the direction of the external magnetic field for magnetization.

When the external magnetic field for magnetization is shut off, the directions of the magnetic moments of the bound magnetic markers and the unbound magnetic markers become random due to Brownian motion. Meanwhile, the nonspecific binding magnetic marker 5 and the magnetic impurities including magnetic impurity 6, which are fixed to the container, maintain the directions of the original magnetic moments.

The signal from the bound markers increases by the magnetization process, but the signal from the magnetic impurities also increases at the same time, and therefore, a more favorable result may be sometimes obtained without performing magnetization by a strong magnetic field.

(c) Next, an external magnetic field 10 for orientation is applied with a magnet 11, and the magnetic markers which were made random are aligned with the direction of the external magnetic field 10 for orientation again. If the strength of the applied magnetic field is made not more than the coercivity of the magnetic markers and the magnetic impurities, the directions of the spins in the magnetic substances included by the magnetic markers and the magnetic impurities do not change. However, by application for a suitable time, the unbound magnetic markers themselves in suspension in the solution are rotated, and the directions of the magnetic moments of the markers can be aligned with the direction of the external magnetic field for orientation. Further, the magnetic markers bound to the substance to be measured are also rotatable with the substance to be measured, and therefore, the magnetic moments of the bound magnetic markers can be also aligned with the direction of the external magnetic field for orientation. It should be noted that the direction of the external magnetic field for orientation does not always have to be equal to that of the external magnetic field for magnetization, but is made in the same direction in this case.

(d) After the external magnetic field for orientation is shut off, the directions of the magnetic moments of the magnetic markers become random again, and therefore, the magnetic signal generated by the specimen decays. The magnetic signal from the unbound magnetic marker 4 decays earlier than that of the bound marker 3. This reason is that the relaxation time of the Brownian rotation is in proportion to the volume of the rotating body. Thus, the magnetic signal from the unbound magnetic marker 4 significantly decays, but if the magnetic signal is measured in the timing in which the magnetic signal from the bound magnetic marker 3 does not decay significantly, the magnetic signal from the bound magnetic marker 3 can be selectively measured. This measured signal is set as a signal 1. The signal 1 also includes the magnetic signals from the nonspecific binding magnetic marker 5 and the magnetic impurities including magnetic impurity 6.

(e) Next, an external magnetic field 12 for orientation with an inversed polarity is applied with a magnet 13. At this time, the magnetic moments of the bound magnetic markers 3 and the unbound magnetic markers 4 in suspension in the solution are oriented to be inversed, but the directions of the magnetic moments of the nonspecific binding magnetic marker 5 and the magnetic impurity 6, which are bound to the container, do not change. The magnetic markers in suspension in the solution can change the directions of the magnetic moments thereof to be inversed with the rotations of the markers themselves, but since the nonspecific binding magnetic marker 5 and the magnetic impurity 6 are fixed to the container, and the directions of the magnetic moments cannot be aligned with the direction of the external magnetic field for orientation with the rotations of the magnetic substances themselves. Further, the strength of the applied external magnetic field for orientation is not more than the coercivity of the magnetic markers and the magnetic impurities, and therefore, the directions of the magnetic moments cannot be aligned with the direction of the external magnetic field for orientation by changing the directions of the spins in the magnetic substances. As a result, the directions of the magnetic moments of the nonspecific binding magnetic marker 5 and the magnetic impurity 6 do not change.

(f) After the external magnetic field for orientation is shut off, the signal of the unbound magnetic marker 4 decays significantly due to the influence of Brownian motion, but the magnetic signals from the specimen are measured in the timing in which the magnetic signals of the bound magnetic markers 3 do not decays significantly. The measurement signal is set as a signal 2. The signal 2 includes the signals of the unbound magnetic markers and the bound magnetic markers of the inversed direction with respect to the signal 1. The signal 2 also includes the magnetic signals from the nonspecific binding magnetic marker 5 and magnetic impurities, but since the external magnetic field for orientation is not so strong as to change the directions of the spins of the magnetic substances included by the nonspecific binding magnetic marker and the magnetic impurity 6, the signals generated by the nonspecific binding magnetic marker and the magnetic impurities and included by the signal 2 are equivalent to these signals generated by the nonspecific binding magnetic marker and the magnetic impurities and included by the signal 1. Accordingly, by subtracting the signal 2 from the signal 1, the magnetic signal components generated by the nonspecific binding magnetic marker and the magnetic impurities fixed to the container can be eliminated.

As above, according to the present invention, the signals generated by the magnetic substances fixed to the container and the magnetic signals generated by the unbound markers in the solution and unbound markers which are not fixed can be separated. As a result, the influence of the signals of the magnetic impurities of the container and the markers adhered to the container, which is conventionally a problem, can be reduced.

Figure 2:
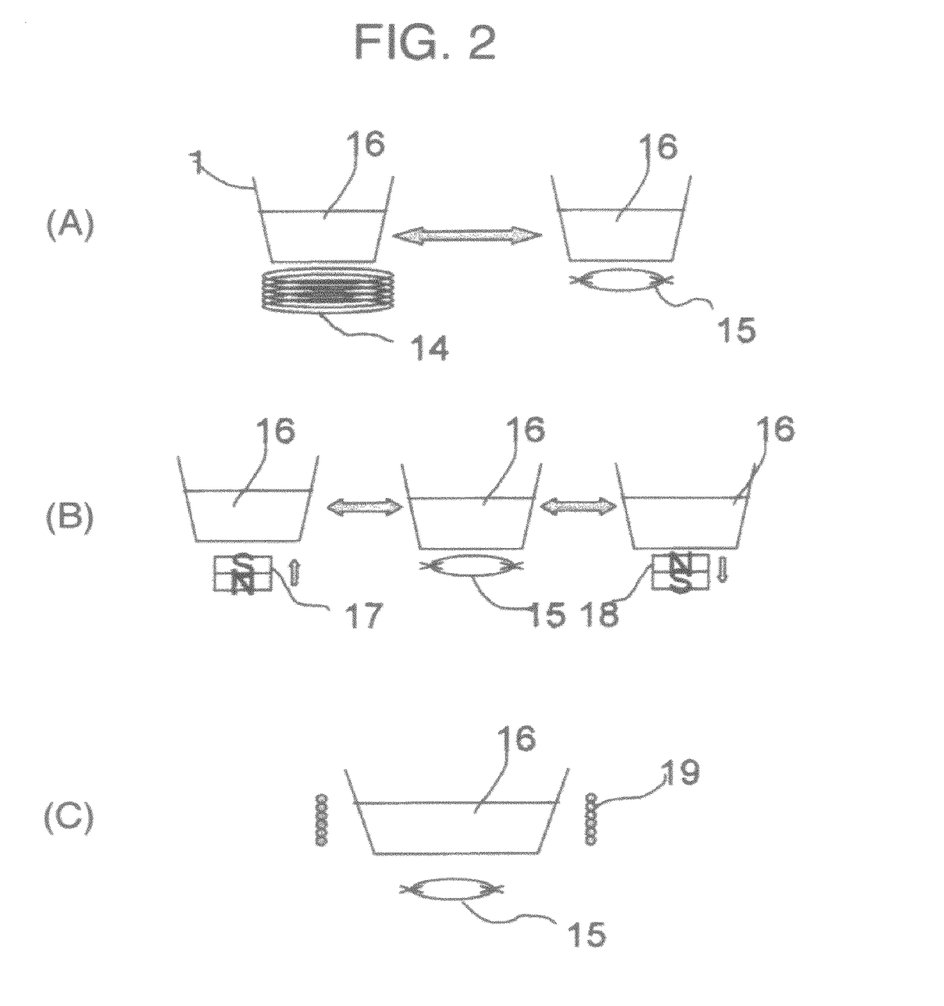
FIGS. 2A to 2C are views showing examples of a system configuration to which the present invention is applicable.

FIGS. 2A to 2C show an example of a device configuration to which the present invention is applicable. As shown in FIG. 2A, when an external magnetic field for orientation is applied with a magnet 14, and thereafter, the magnetic signal of a specimen 16 is measured with a magnetic sensor 15, the external magnetic field for orientation in the reverse direction can be easily applied by reversing the electric current which is passed to the magnet 14, and the method of the present invention can be applied. As shown in FIG. 2B, magnets 17 and 18 for applying external magnetic fields for orientation with two different polarities are prepared, after the external magnetic field is applied and the specimen is oriented in an certain direction with one magnet 17, the magnetic signals are measured, then, after the external magnetic filed in the reverse direction is applied and the specimen is oriented with the other magnet 18 with the reverse polarity, the magnetic signals are measured, whereby the method of the present invention can be carried out. The magnets 17 and 18 may be permanent magnets or electromagnets, but in any case, the influence of a fringing field needs to be prevented. Contrivance such as the method for applying parallel magnetic fields to the specimen with the upper and lower two magnets, and application of the pulse magnetic field only when the specimen is on the coil is needed. In the methods in FIGS. 2A and 2B, the specimen 16 is moved, but as shown in FIG. 2C, with the method in which the magnetic field is applied by an electromagnet 19 in the state in which the specimen 16 is placed on the magnetic sensor 15, and after the electric current which is passed to the electromagnet is cut off, the measurement is performed, the present invention can be carried out by performing measurement by reversing the electric current which is passed to the electromagnet 19.

As above, according to the present invention, the signals from the magnetic substances fixed to the container and the magnetic signals from the bound markers and unbound markers can be separated. As a result, the influence of the signals of the magnetic impurities of the container and the markers bound to the container which is conventionally a problem can be reduced, and measurement with high sensitivity and high accuracy is made possible. Further, the influence of the magnetic impurities of the container can be reduced by the present invention, manufacture and quality control of the containers are facilitated. According to circumstances, a special process and production apparatus required for production of containers with a low magnetic impurities concentration are expected to be unnecessary. Further, occurrence of an erroneous measurement result by the magnetic impurities adhering to the container at the time of measurement can be prevented. If this technique is applied to the inspection of, for example, immunoglobulin, hormone, a tumor marker or the like, quick and highly sensitive inspection with a very small quantity of specimen can be expected. Further, blood culturing and bacterial culturing which take much time until determination are required in the inspection of pathogenic bacterium of an infectious disease, food poisoning and the like, but there is the possibility of making the inspection of pathogenic bacterium without culturing owing to the magnetic detection using the present technique, and the present technique is expected to be able to contribute to quick inspection of pathogenic bacterium.

Other objects, features and advantages of the invention will become apparent from the following description of the embodiments of the invention taken in conjunction with the accompanying drawings.

DETAILED DESCRIPTION OF THE INVENTION

In the following description, magnetic marker (an antibody marked with magnetic nano particles having a residual magnetic signal) is used, and a magnetic signal from a specimen which reacts with an inspection reagent is detected with a 1st order SQUID gradiometer. Embodiments of the present invention will be described with a magnetic bio-inspection system as an example. The following disclosure is only an embodiment of the present invention, and does not intend to limit the technical range of the present invention in any way.

Embodiment 1

Figure 3:
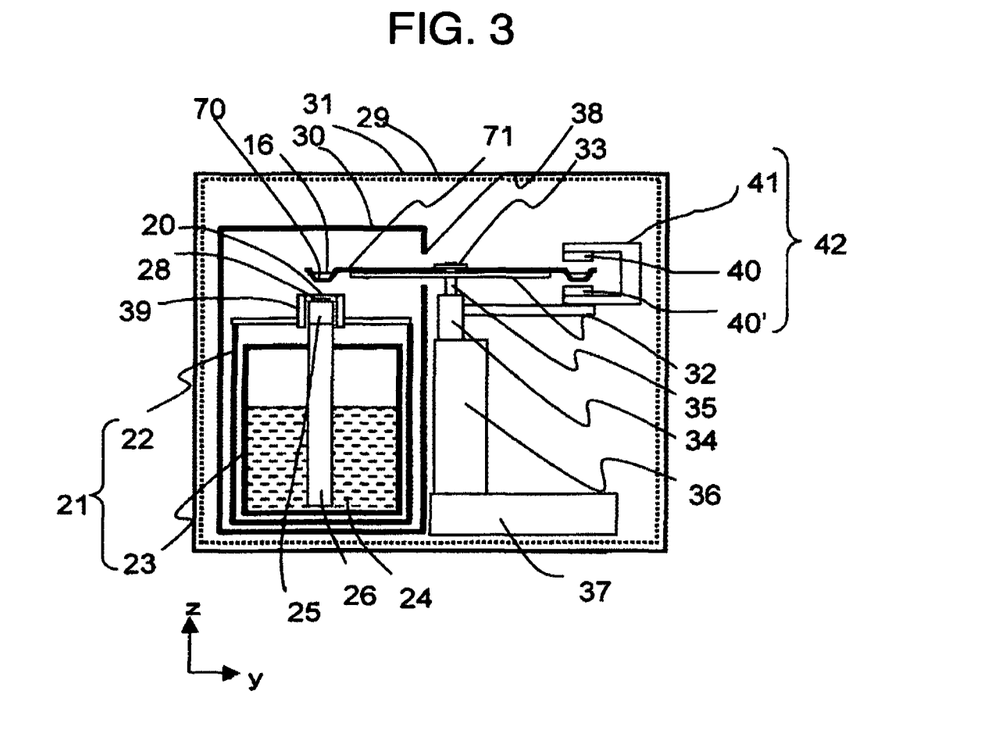
FIG. 3 is a sectional view showing the configuration of a magnetic bio-inspection system used in an embodiment of the present invention.

FIG. 3 is a sectional view showing the configuration of a magnetic bio-inspection system which is one embodiment of the present invention. In order to reduce input of ambient magnetic noise to a SQUID 28, the SQUID and a cooling container 21 for cooling the SQUID are surrounded by an electromagnetic shield 29 and magnetic shields 30 and 31. The magnetic shield 29 is constituted of a metal material with low electric resistance such as aluminum, and the magnetic shields 30 and 31 are constituted of a material with a high magnetic permeability such as permalloy. A cutout hole 38 for inserting a specimen container 71 therein is formed in a part of the magnetic shield 30.

Figure 4:
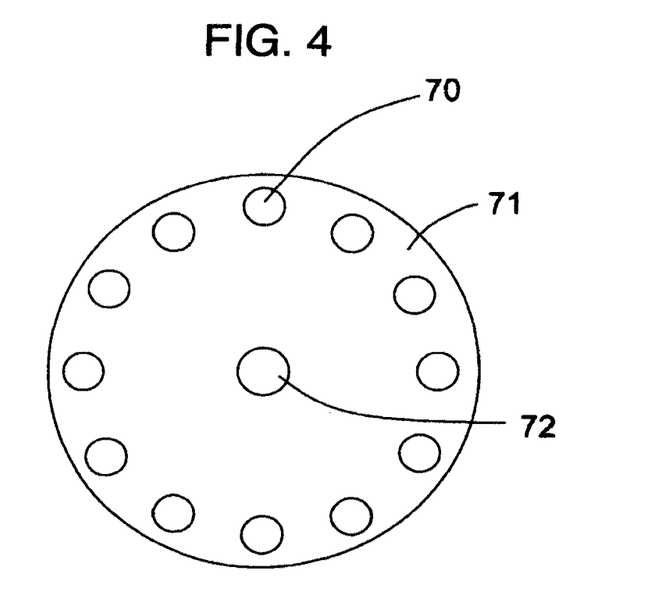
FIG. 4 is a schematic view of a specimen container used in the embodiment.

The specimen container 71 is fixed to a rotating shaft 35 by a fixing screw 33, on a non-magnetic disk-shaped specimen table 32. FIG. 4 shows a schematic view of the specimen container 71 used in the experiment. The container is made of a non-magnetic material such as a resin. The container 71 is circular, has 12 well portions 70 each in the shape of a circular truncated cone on the outer circumferential portion, and has in its center a hole 72 for being fixed to the system. The diameter of the bottom surface of the well portion is 5 mm. A specimen 16 is put in the well portions, and the respective wells are expressed by container numbers 1 through 12. The specimen table 32 rotates by the rotating shaft 35 connected to a rotary mechanism 34. The rotary mechanism 34 is movable in a three-dimensional direction on moving stages 36 and 37, and by movement of the rotary mechanism 35, a part of the specimen container 71 is moved to the inside of the magnetic shield 30 through a cutout hole 38, and position adjustment is performed so that the bottom surface of the well portion 70 and a sapphire window 20 are close to each other.

In order to make the distance between the specimen 16 and the SQUID 28 small and enhance the detection sensitivity for the magnetic signals generating from the specimen and spatial resolution, the SQUID 28 is placed at a lower portion of the sapphire window 20. By the specimen container 71 rotating, a plurality of specimens 16 sequentially pass above the SQUID 28, and the magnetic signals at this time are measured. The system is normally used at 20 to 60 rpm, measures the signals of 40 to 100 rotations, and performs signal averaging processing to improve the signal-to-noise (SN) ratio. The sapphire window 20 is fixed to a nonmagnetic cylindrical component 39, and can be positioned in the vertical direction. Further, at the position opposed to the SQUID, a magnetizing mechanism 42 for generating an external magnetic field for orientation is installed. The magnetizing mechanism 42 is configured by two magnets 40 and 40' and a yoke 41, and the magnetizing direction of the two magnets are aligned so that a parallel magnetic field in the vertical direction occurs between the two magnets. By disposing the magnetizing mechanism 42 upside down vertically, the direction of the external magnetic field for orientation can be reversed. The strength of the applied magnetic field is several hundred gausses.

The Superconducting quantum interference device 28 is placed in a vacuum insulation layer of the cooling container 21 in which a space between an outer tank 22 and an inner tank 23 is the vacuum insulation layer, and is indirectly cooled by liquid nitrogen 24 via a copper rod 26 with a high thermal conductivity and a sapphire rod 25. The outer tank 22 and the inner tank 23 of the cooling container are constituted by a nonmagnetic material such as SUS and FRP. By interposing the sapphire rod 25 between the SQUID 28 and the copper rod 26, the effect of reducing the influence of the magnetic noise occurring from the copper rod 26 is provided.

Figure 5:
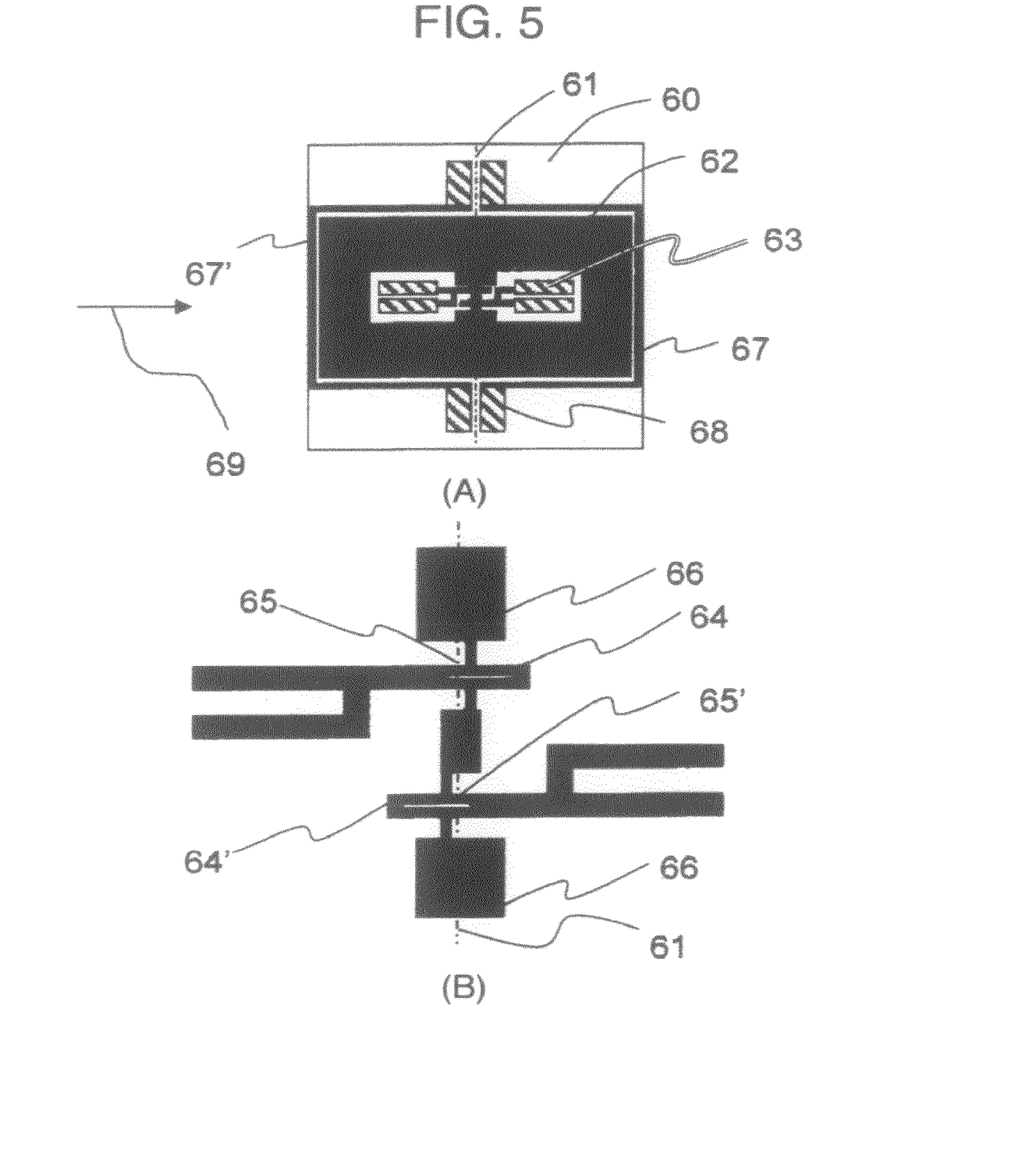
FIGS. 5A and 5B are views explaining the relationship of the magnetizing direction of a specimen and the detected magnetic signal waveform in the case of using a 1st order SQUID gradiometer.

In the immunoassay system of the present embodiment, as the SQUID 28, a high-temperature superconductor SQUID gradiometer is used. FIGS. 5A and 5B are plane views schematically showing the configuration of the high-temperature superconductor SQUID gradiometer. FIG. 5A is a view showing the entire configuration, and FIG. 5B is an enlarged view of a central portion. A pickup coil 62 and a SQUID ring 64 are produced by working a high-temperature superconductor material such as $YBa_2Cu_3O_x$ which is formed on a bicrystal substrate 60 of a structure in which the single crystals of $SrTiO_3$, MgO and the like are bonded on a bicrystal joint surface 61 by shifting the crystallographical orientations. The SQUID ring 64 is across the bicrystal joint surface 61 formed on the bicrystal substrate 60, and a grain boundary Josephson junction 65 is formed on a superconductor thin film formed on the bicrystal joint surface 61. As a result, two grain boundary Josephson junctions 65 are formed at the SQUID ring 64. In the SQUID used this time, two SQUID rings 64 and 64' bound to the same pickup coil are formed on one substrate, and the alternative of them, the SQUID with better characteristics is used in the experiment.

The pickup coil 62 constitutes a gradiometric pickup coil in the shape of the FIG. 8 having two loops with each side of 5 mm, and when a magnetic flux is input to the pickup coil 62, a difference amount of induced currents occurring to the respective loops of the two loops flows into the SQUID rings 64 and 64' via the central portions 66 of the pickup coil. The current is detected as a magnetic flux. A feedback coil 67 is formed on the substrate 60 by patterning so as to surround one loop of the pickup coil 62. One of two feedback coils 67 and 67' is used. Where connection of wiring is required, gold wiring pads 63 and 68 are patterned on the superconductor thin film. The wiring pad 63 is electrically connected to the SQUID ring 64, and the wiring pad 68 is electrically connected to the feedback coil 67.

Before measuring the specimen, the magnetic signal of the nonmagnetic specimen container 71 shown in FIG. 4 is measured. The specimen container is brought close to a neodymium magnet (surface magnetic flux density 250 mT) in the state in which a specimen was not put in the well portion 70 and the magnetic impurities included in the vacant specimen container is magnetized, after which, the magnet was moved away from the specimen container.

The specimen container was fixed to the disk-shaped specimen table 32 of the system for detection shown in FIG. 3, and the change in the magnetic signal occurring from the container is measured. First, measurement is performed in the state in which the magnetizing mechanism 42 is placed so that the south pole is on the upper side, and a signal 1 is obtained. Next, in the state in which the magnetizing mechanism 42 is placed so that the north pole is on the upper side, the measurement is performed, and a signal 2 is obtained.

Figure 6:
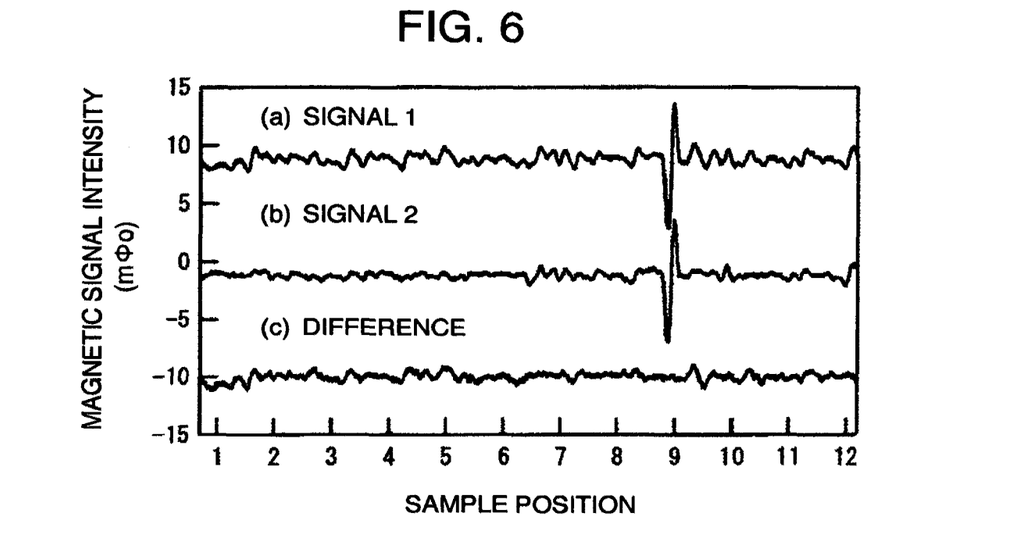
FIG. 6 shows magnetic signal waveforms of a vacant specimen container.

FIG. 6 shows the time waveforms of the signal 1 and signal 2 obtained by measurement and the difference of them. At the position of container number 9 of the signal 1, a large change of the magnetic signal of an amplitude of about 10 m$\phi$0 is observed. Since, the signal cannot be removed even when the container is wiped with alcohol, this is considered to be the signal from the magnetic impurities included in the container. If the magnetizing direction of the magnetic impurities is reversed when the external magnetic field for orientation is reversed, the magnetic signal reversed in the vertical direction should be detected, but the same signal is observed in the signal 2. As a result, in the difference by subtracting the signal 2 from the signal 1, the change of the magnetic signal at the position of container number 9 is cancelled. Further, small variations of the magnetic signals in the vicinity of container number 7 and in the vicinity of container number 10 in FIG. 6 also have small amplitudes in the difference, and it can be confirmed that the method of the present invention is effective for removal of noise signal of the container.

Figure 7:
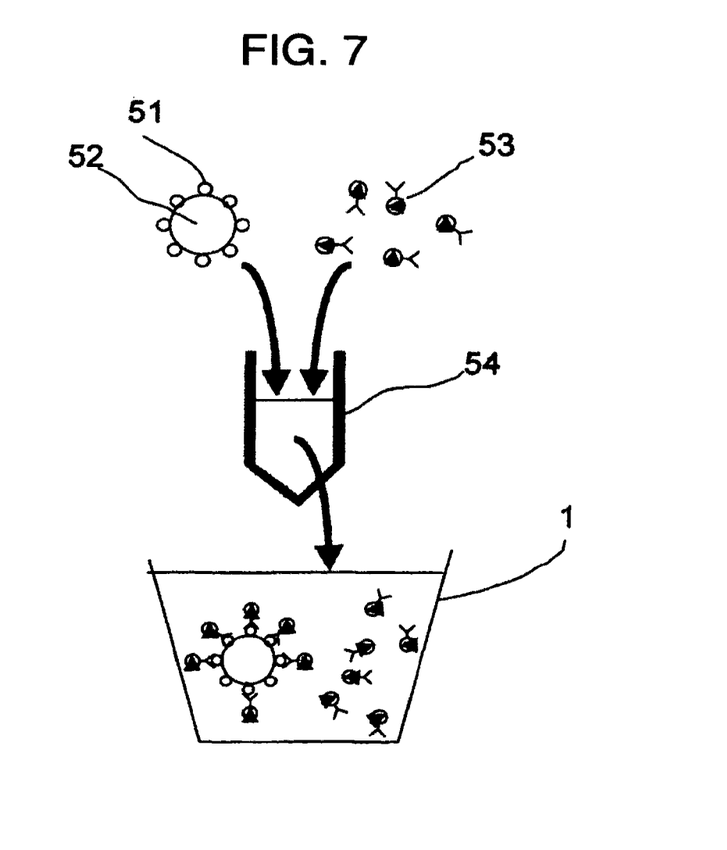
FIG. 7 is a view for explaining a method for producing a specimen in embodiment 1.

Next, the effect of the present invention when the actual specimen is measured will be described. In this embodiment, a polymer bead 52 with biotin 51 bound to the surface is used as a substance to be measured as shown in FIG. 7. The particle size of the polymer bead is 1 μm.

As a magnetic marker 53, a commercially available streptavidin conjugated magnetic marker (made by R&D System Corporation) is used. Since streptavidin is specifically bound to biotin, the biotin conjugated polymer particle can be detected by the magnetic marker.

First, 100 μl of a magnetic marker solution diluted to a concentration of 0.1 mg/ml and 40 μl of a polymer bead solution containing 10000 polymer beads 52 are put into an micro test tube 54 of a capacity of 2 ml, and are stirred with a vortex every five minutes to cause reaction for 15 minutes. Thereafter, in order to magnetize the magnetic marker, the Eppen tube is moved close to a neodymium magnet, and a magnetic field of about 1500 gausses is applied. Thereafter, 35 μl of the solution after reaction is added to each of the three well portions 70 of the nonmagnetic specimen container 71 showing the magnetic signal waveform in FIG. 6.

As in the measurement of the vacant specimen container, after the specimen and the specimen container are moved close to the neodymium magnet to be magnetized to saturated magnetization, measurement is performed in the state in which the magnetizing mechanism 42 is placed so that the south pole is on the upper side and in the state in which the magnetizing mechanism 42 is placed so that the north pole is on the upper side, and a signal 1 and a signal 2 are obtained.

Figure 8:
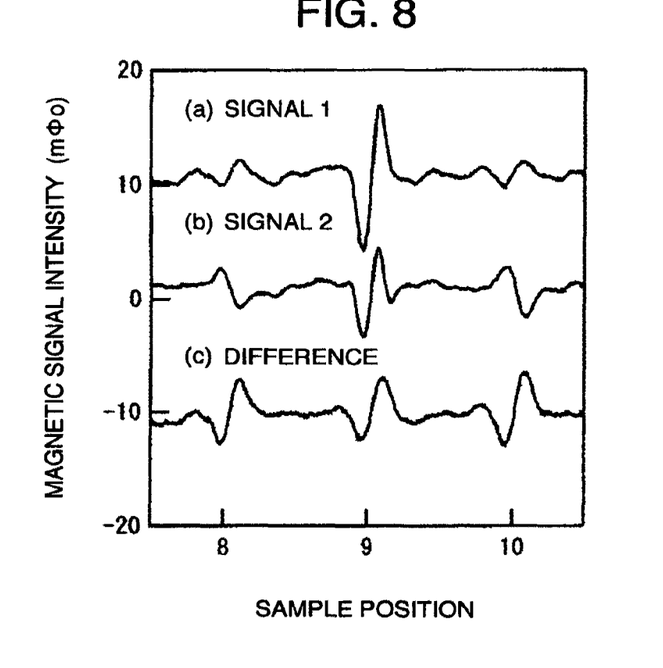
FIG. 8 shows a measurement result of a polymer bead specimen and application result of the present invention.

FIG. 8 shows the magnetic signal waveforms of the three spots that are container numbers 8 to 10. (A) represents the signal 1, (B) represents the signal 2 and (C) represents a difference. The magnetic signal intensity of the specimen is defined as the maximum amplitude of the signal at each of the specimen positions. Each of the three spots has the same specimen, and the same magnetic signal intensity should be observed ideally. However, at the position of container number 9 of the signal 1, the signal of the magnetic impurities shown in FIG. 6 exists, and therefore, large magnetic signal intensity is shown. In the signal 2 measured by reversing the external magnetic field for orientation, the signal waveforms of container numbers 8 and 10 are reversed in the vertical direction, and this shows that the magnetizing direction of the magnetic marker bound to the polymer bead that is a measurement target is reversed by reversal of the external magnetic field for orientation. The signal waveform of container number 9 is not reversed, and this is due to the influence of the magnetic impurities which is not reversed with the external magnetic field for orientation as shown in FIG. 6. Like this, with the normal measurement signal, correct measurement is difficult by being influenced by the container noise. However, by finding the difference of the two measurement signals by using the method of the present invention, the influence of the magnetic impurities of the container can be removed. As is understood from the difference of FIG. 8(C), substantially the same magnetic signal intensities are obtained from the three specimens of container numbers 8 to 10. Further, by finding the difference, the signal intensity increases to be about doubled. It is found out that the variations of the measurement signals observed not only from the magnetic impurities at the position of the container number 9, but also between the specimens 8 and 9 and the specimens 9 and 10 are suppressed. From the above result, according to the present invention, it can be confirmed that the influence of the container noise is reduced, and the magnetic signal intensity from the measurement target substance is increased, whereby the SN ratio can be remarkably improved.

Figure 9:
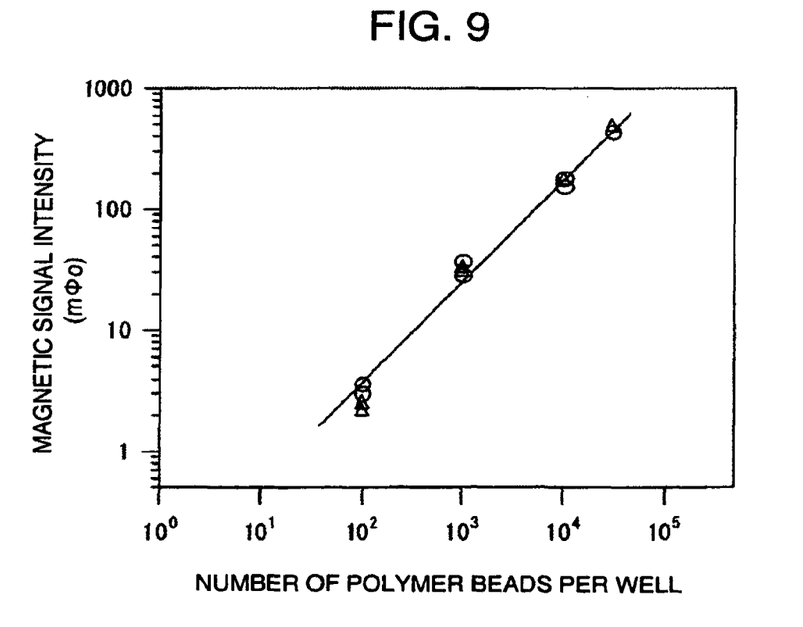
FIG. 9 shows the relationship of magnetic signal intensity and the number of polymer beads.

FIG. 9 shows the relationship (calibration curve) of the obtained magnetic signal intensity and the number of polymer beads. The magnetic signal monotonously changes in accordance with the number of polymer beads. By using this curve as the calibration curve, the number of polymer beads in the specimen can be found from the measured magnetic signal. The present embodiment shows that the number of polymer beads can be measured by using the magnetic marker conjugated with avidin which is specifically bound to biotin for the polymer bead 52 with the biotin 51 bound to the surface that is the measurement target substance.

When the measurement target is a pathogenic bacteria, the magnetic signal with the intensity corresponding to the number of pathogenic bacterium can be measured by using a magnetic marker conjugated with the antibody specifically bound to protein, a sugar chain and the like existing on the surface of the pathogenic bacterium, and not only the presence and absence of the pathogenic bacteria but also the number of the pathogenic bacterium can be found from the magnetic signal. Therefore, this can be used for the inspection of infectious disease, food poisoning and the like.

Embodiment 2

Figure 10:
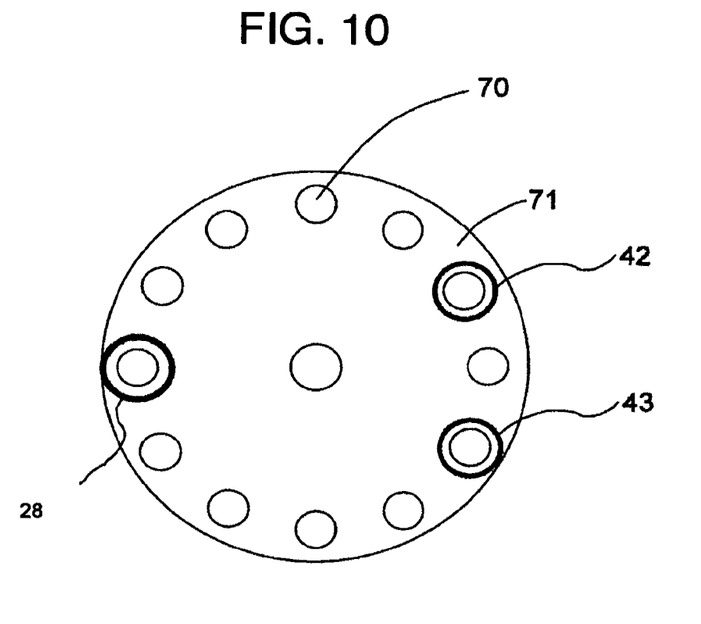
FIG. 10 is a view for explaining the disposition of magnetizing mechanisms and a SQUID in embodiment 2.

In the present embodiment, two magnetizing mechanisms 42 and 43 with reverse polarities from each other are placed on the circumference on which the specimen container 71 rotates as shown in FIG. 10. In embodiment 1, the direction of the external magnetic field for orientation is reversed by disposing the magnetizing mechanism 42 in the vertically inverted position, but in the present embodiment, the direction of the external magnetic field for orientation which is applied to the specimen immediately before measurement can be reversed by reversing the rotating direction of the specimen container 71. The specimen passes through the two magnetizing mechanisms, but the magnetic moments of the specimen are aligned in the direction of the magnetic field of the magnetizing mechanism which the specimen passes immediately before measurement.

As for the two magnetizing mechanisms 42 and 43, with the position of the SQUID 28 set at zero degrees, the magnetizing mechanism 42 is installed at the position at 150 degrees in a clockwise direction, and the magnetizing mechanism 43 is installed at the position at 150 degrees in a counterclockwise direction. The magnetizing mechanism 43 has the same structure as the magnetizing mechanism 42, but the direction of its magnetic field is opposite. The magnetic flux density at the specimen position is several hundred gausses. As in embodiment 1, the specimen in which the biotin conjugated polymer beads are reacted with the magnetic marker is used. After the specimen and the specimen container are moved close to a neodymium magnet to be magnetized to the saturated magnetization first, the specimen container is initially rotated clockwise at a speed of 20 rpm to measure the magnetic signal. In this case, the specimen passes above the SQUID after passing above the magnet with the south pole on the upper side. The signals of 40 rotations are measured, and signal averaging processing of 40 times is performed (signal 1). Next, the specimen is rotated counterclockwise and the magnetic signals are measured. In this case, the specimen passes above the SQUID after passing above the magnet with the north pole on the upper side, and therefore, the magnetic markers in suspension are oriented in the reverse direction. The signals of 40 rotations are measured, and signal averaging processing of 40 times is performed (signal 2). When the rotating direction is reversed, the relative positional relationship of the time waveform of the measured magnetic signal, the SQUID and the specimen is also reversed. Thus, after the signal 2 is laterally reversed, the difference from the signal 1 is found.

As a result, as in embodiment 1, it can be confirmed that the magnetic signal from the magnetic marker solution including the aggregated magnetic marker that is a substance not to be measured increases to be about doubled in the difference, and it can be also confirmed that the signal from the nonspecific binding magnetic marker or the dry magnetic marker corresponding to the magnetic impurities significantly decreases in the difference.

Embodiment 3

Figure 11:
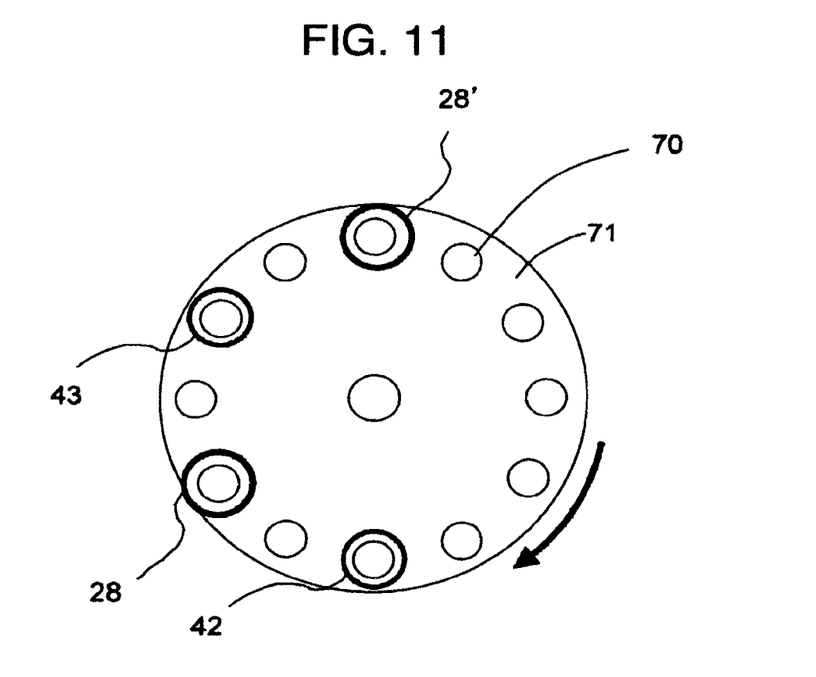
FIG. 11 is a view for explaining the disposition of magnetizing mechanisms and SQUIDs in embodiment 3.

In the present embodiment, as shown in FIG. 11, on the circumference on which the specimen container 71 rotates, the two magnetizing mechanisms 42 and 43 with reverse polarities from each other are placed, and two SQUIDs 28 and 28' are further placed. In embodiment 2, by reversing the rotating direction of the specimen container 71 by using the two magnets, the direction of the external magnetic field for orientation which is applied to the specimen immediately before measurement is reversed, but in the present embodiment, by disposing the two magnetic sensors and by rotating the specimen in the arrow direction in FIG. 11, the magnetic signal after passing the magnetizing mechanism 42 can be measured with the SQUID 28, and the magnetic signal after passing the magnetizing mechanism 43 can be measured with the SQUID 28'.

The magnetizing mechanism 43 has the same structure as the magnetizing mechanism 42, but the direction of its magnetic field is in the reverse direction. The magnetic flux density at the specimen position is several hundred gausses. As in embodiments 1 and 2, the specimen in which the biotin conjugated polymer beads and the magnetic marker are reacted is used. After the specimen and the specimen container are moved close to a neodymium magnet to be magnetized to saturated magnetization first, the specimen container is rotated clockwise at a speed of 20 rpm to measure the magnetic signals (two systems) detected with the two SQUIDs at the same time. The signals of 40 rotations are measured, and signal averaging processing of 40 times is performed. Subtraction is performed for the magnetic signals measured with the two SQUIDs thus measured by matching the timings in which the specimen passes the SQUIDs. As a result, as in embodiments 1 and 2, it can be confirmed that the magnetic signal from the magnetic marker solution including the aggregated magnetic marker that is a substance not to be measured increases to be about doubled in the difference, and it can be also confirmed that the signal from the nonspecific binding magnetic marker or the dry magnetic marker corresponding to the magnetic impurities significantly decreases in the difference.

Embodiment 4

Figure 12:
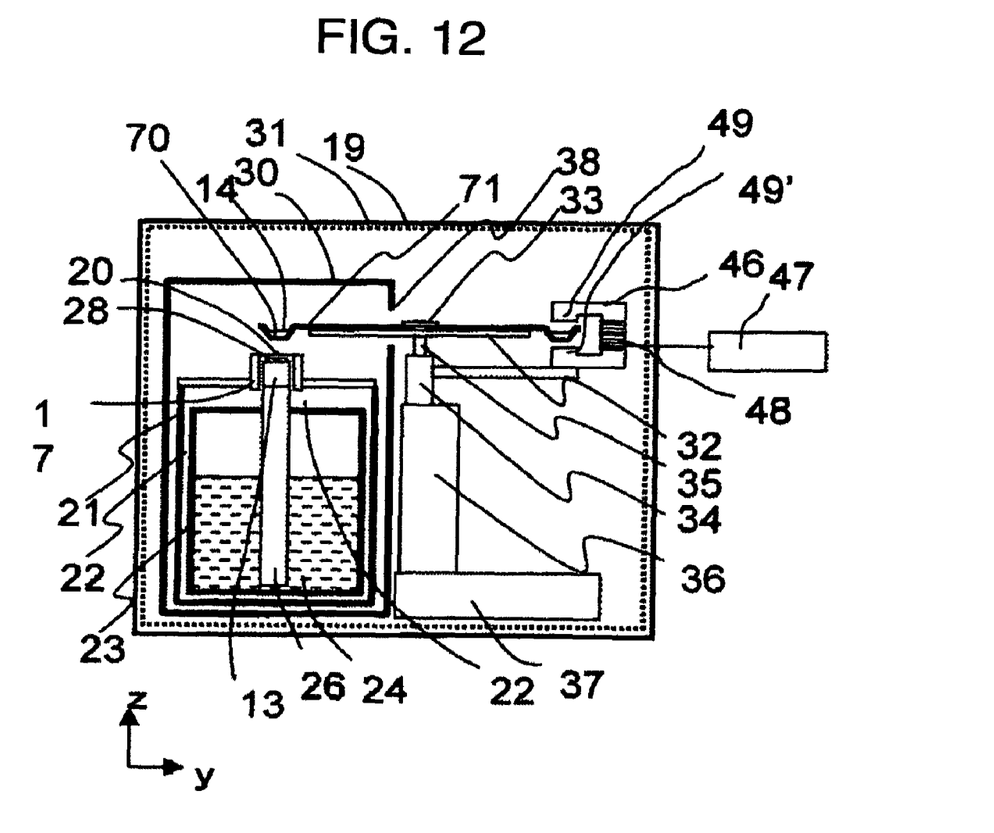
FIG. 12 is a sectional view showing the configuration of a magnetic bio-inspection system used in embodiment 4.

In the present embodiment, a magnetizing mechanism 46 using an electromagnet is used. FIG. 12 shows a schematic view of a sectional structure of a measurement system which is used. A coil 48 of the magnetizing mechanism 46 is connected to a power source 47, and can pass a pulse current in the timing at which a specimen 14 passes between magnetic poles 49 and 49' of the magnetizing mechanism 46. The direction of the external magnetic field for orientation which is applied can be reversed by reversing the direction of the current. Further, the magnetic field for magnetization can be applied by passing a large current.

In the present embodiment, as in embodiments 1 to 3, measurement is performed by using the specimen in which the biotin conjugated polymer beads and the magnetic marker are reacted.

After 35 μl of the reaction solution of the biotin conjugated polymer beads and the magnetic marker is put into the well portion 70 of the specimen container 71, a current with pulse width of 1 to 10 ms is passed to the coil 48 in the timing at which the specimen passes between the magnetic poles 49 and 49' of the magnetizing mechanism 46 while the specimen container is rotated clockwise at 20 rpm. The applied magnetic field strength is about 500 to 1000 gausses.

Next, the strength of the pulse magnetic field to be applied is reduced to 100 gausses, and the magnetic signal is measured with the SQUID 28. The signals of 40 rotations are measured, and signal averaging processing of 40 times is performed (signal 1). Next, the direction of the current is reversed, and with the magnetic field of 100 gausses applied in the reverse direction, the signals of 40 rotations are also measured, and signal averaging processing of 40 times is performed (signal 2). By subtracting the signal 2 from the signal 1, the difference signal waveform is found.

As a result, as in embodiments 1 to 4, it can be confirmed that the magnetic signal from the magnetic marker solution including the aggregated magnetic marker that is a substance not to be measured increases to be about doubled in the difference, and it can be also confirmed that the signal from the nonspecific binding magnetic marker or the dry magnetic marker corresponding to the magnetic impurities significantly decreases in the difference.

All of the four embodiments described here report the biotin conjugated polymer particles, but can be applied to the reactions in which the measurement target substance in the solution binds with the magnetic marker or forms aggregate with the magnetic marker. Showing some examples, as in FIG. 13A, a polymer particle 81 with a primary antibody 84 fixed to the surface is used, an antigen 82 that is the measurement target substance is reacted with a magnetic marker 83 conjugated with a secondary antibody which binds with the antigen, and the aggregate of the primary antibody-antigen-magnetic marker is formed, whereby detection of the antigen becomes possible by applying the present method. The conventional optical method requiring washing requires antibody for fixing for fixing the specimen to the container, and therefore, has the problem that the cost of the container is high, and requires time and effort to fix the antibody for fixing for oneself. By forming the aggregate of the primary antibody-antigen-magnetic marker is formed on the polymer bead surface as shown in FIG. 11A, the method of the present invention can be applied, and labor and cost required for preparation of the antibody for fixing can be reduced.

Figure 13:
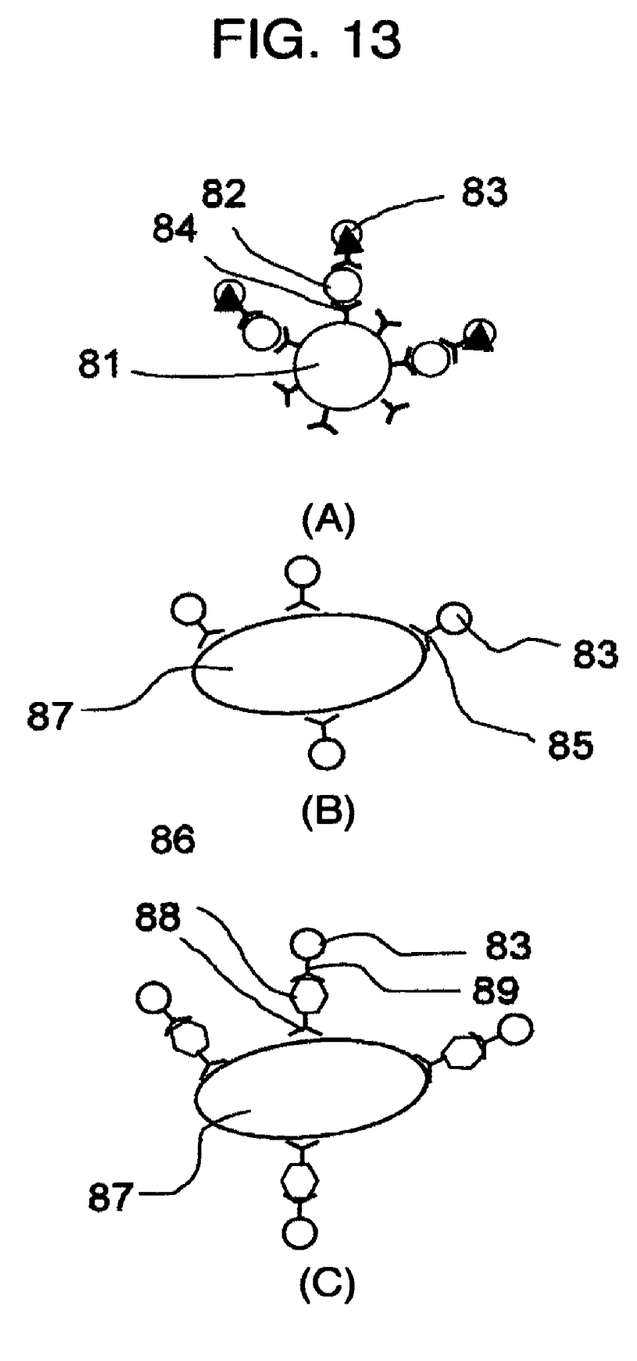
FIGS. 13A to 13C show examples of reactions to which the present invention is applicable.

Further, as in FIG. 13B, the present invention can be applied to detection of a cell and bacteria by using the magnetic marker 83 conjugated with an antibody 85 which selectively binds with a specific protein on a cell or a cell membrane surface of a bacteria 87. As compared with protein, a cell and a bacteria themselves are large. Therefore, even if the cell and the bacteria are not fixed to the polymer bead surface, the Brownian rotation relaxation time of the magnetic marker bound to the cell or the bacteria in suspension is sufficiently longer than the Brownian rotation relaxation time of the unbound magnetic marker. Therefore, by using the difference in the relaxation time, the magnetic signal from the bound magnetic marker can be selectively measured, and at the same time, the method of the present invention is applicable.

Further, as in FIG. 11C, the present invention can be applied to detection of a cell and a bacteria using an antibody 88 which is bound to a specific protein on the cell membrane surface conjugated with a biotin 86, and the magnetic marker 83 conjugated with an avidin 89. In this case, there is provided the advantage that if the magnetic marker conjugated with the avidin 89 is prepared, various cells and pathogenic bacterium can be measured by using an antibody which is bound to a specific protein on the cell membrane surface conjugated with the biotin 86 which is commercially available.

Further, the SQUID is used as the magnetic sensors in the present embodiments, but the same effect can be expected in the case of using magnetic sensors such as a giant magnetoresistance sensor, a magnetoresistance sensor, an optical pumping flux meter, a flux-gate flux meter, and a Hall element.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A method for detecting a target substance by binding magnetic particles to the target substance in a solution contained in a container and detecting with a magnetic sensor, a magnetic signal generated by the magnetic particles, comprising the steps of:
   a first step of applying a first external magnetic field for orientation to the solution as a specimen including the target substance bound to the magnetic particles;
   a second step of shutting off said first external magnetic field for orientation to detect a first magnetic signal;
   a third step of applying to the solution a second external magnetic field for orientation which second external magnetic field has an inverse polarity, as compared with the first external magnetic field and a strength of which second external magnetic field is not more than coercivity of the magnetic particles and coercivity of magnetic impurities;
   a fourth step for shutting off said second external magnetic field for orientation to detect a second magnetic signal; and
   a fifth step for obtaining a difference between the first magnetic signal and the second magnetic signal to detect the target substance with eliminating at least one of (1) a magnetic influence of the magnetic particles adhering to the container and (2) the magnetic impurities adhering to the container.

2. The method according to claim 1, further comprising a preliminary step of applying to the solution including the magnetic particles and the target substance bound to the magnetic particles an external magnetic field for magnetization before the first step, wherein a strength of the external magnetic field for magnetization is greater than strengths of the first and second external magnetic fields for orientation.

3. The method according to claim 1, wherein at least one of the first and second steps includes a step of applying to the solution corresponding at least one of the first and second external magnetic fields at a first position of the container, and at least one of the second and forth steps includes another step of detecting corresponding at least one of first and second magnetic signals after the container is moved from the first position to a second position distant from the first position.

* * * * *